United States Patent
Baxter

(10) Patent No.: US 6,465,423 B1
(45) Date of Patent: *Oct. 15, 2002

(54) ACID-LABILE SUBUNIT (ALS) OF INSULIN-LIKE GROWTH FACTOR BINDING PROTEIN COMPLEX

(75) Inventor: Robert Charles Baxter, Glebe (AU)

(73) Assignee: Central Sydney Area Health Service, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/282,089

(22) Filed: Mar. 30, 1999

Related U.S. Application Data

(62) Division of application No. 08/459,209, filed on Jun. 2, 1995, now Pat. No. 5,936,064, which is a division of application No. 08/213,402, filed on Mar. 14, 1994, now Pat. No. 5,561,046, which is a division of application No. 07/989,962, filed on Dec. 11, 1992, now Pat. No. 5,324,820, which is a continuation of application No. 07/646,779, filed on Jan. 18, 1991, now abandoned.

(30) Foreign Application Priority Data

Jul. 15, 1988 (AU) ................................. PI9134
Mar. 23, 1989 (AU) ................................. PJ3350

(51) Int. Cl.[7] .............................................. A61K 38/00
(52) U.S. Cl. ................................ 514/2; 514/12; 514/21; 530/350
(58) Field of Search .............................. 514/2, 12, 21; 530/350

(56) References Cited

U.S. PATENT DOCUMENTS

| | | | |
|---|---|---|---|
| 5,258,257 A | | 11/1993 | Baxter et al. |
| 5,324,820 A | * | 6/1994 | Baxter ........................ 530/350 |
| 5,328,891 A | | 7/1994 | Baxter |
| 5,736,511 A | * | 4/1998 | Baxter ........................ 514/12 |
| 5,849,687 A | * | 12/1998 | Baxter ........................ 514/2 |

FOREIGN PATENT DOCUMENTS

| | | |
|---|---|---|
| EP | 294021 | 12/1988 |
| WO | WO 89/08667 | 9/1989 |
| WO | WO 89/09792 | 10/1989 |

OTHER PUBLICATIONS

Baxter and Cowell, Diurnal Rhythm of Growth Hormone–Independent Binding Protein for Insulin–Like Growth Factors in Human Plasma, *J. Clin. Endo. & Metab.* 65(3):432–440 (1987).

Baxter & Martin, "Binding Proteins for Insulin–Like Growth Factors in Adult Rat Serum. Comparison With Other Human and Rat Binding Proteins" *Biochem. & Biophys. Res. Comm.* 147(1):408–415 (1987).

Baxter & Martin, "Radioimmunoassay of Growth–Hormone–dependent Insulinlike Growth Factor Binding Protein in Human Plasma" *J. Clin. Invest.* 78:1504–1512 (1986).

Baxter et al., "Growth Hormone–Dependent Insulin–Like Growth Factor (IGF) Binding Protein from Human Plasma Differs from Other Human IGF Binding Proteins" *Biochem. & Biophys. Res. Comm.* 139(3):1256–1261 (1986).

Baxter et al., "High Molecular Weight Insulin–like Growth Factor Binding Protein Complex" *Journal of Biological Chemistry* 264(20):11843–11848 (1989).

Baxter, Robert C., "Characterization of the Acid–Labile Subunit of the Growth Hormone–Dependent Insulin–Like Growth Factor Binding Protein Complex" *J. Clin. Endo. & Metab.* 67(2):265–272 (1988).

Baxter, Robert C., "Circulating Levels and Molecular Distribution of the Acid–Labile (.alpha.) Subunit of the High Molecular Weight Insulin–Like Growth Factor–Binding Protein Complex" *J. Clin. Endo. & Metab.* 70(5):1347–1353 (1990).

Baxter, Robert C., "The Insulin–Like Growth Factors and Their Binding Proteins" *Comp. Biochem. Physiol.* 91B(2):229–235 (1988).

Brewer et al., "Cloning, Characterization, and Expression of a Human Insulin–Like Growth Factor Binding Protein" *Biochem. & Biophys. Res. Comm.* 152(3):1289–1297 (1988).

Cunningham et al., "The Complete Amino Acid Sequence of .beta..delta.02–Microglobulin" *Biochemistry* 12(24):4811–4821 (1973).

Czech & Massague, "Subunit structure and dynamics of the insulin receptor" Fed. Proc. 41(11):2719–2723 (1982).

Daughaday et al., "Characterization of Somatomedin Binding in Human Serum by Ultracentrifugation and Gel Filtration" *J. Clin. Endo. & Metab.* 55(5):916–921 (1982).

Furlanetto & Van Wyk, "Studies on the Somatomedin–C Binding Protein: Evidence for a Heterologous Subunit Structure" *Proceedings–Endocrine Soc.*, 60th Annual Meeting (abstract 412) (Jun. 1978).

(List continued on next page.)

*Primary Examiner*—Lorraine Spector
*Assistant Examiner*—Eliane Lazar-Wesley
(74) *Attorney, Agent, or Firm*—Richard F. Trecartin; David C. Foster; Dorsey & Whitney LLP

(57) ABSTRACT

The acid-labile sub-unit (ALS) of insulin like growth factor binding protein complex in biologically pure form is described.

ALS has a molecular weight between 80–115 kd as determined by SDS polyacrylamide gel electrophoresis, run under reducing conditions; and a partial N-terminal amino acid sequence as follows:

Gly
   AspProGlyThrProGlyGluAlaGlu G-
      lyProAlaCysProAlaAlaCysAla wherein the first amino acid may be Gly or Ala.

Also described are methods of producing ALS, compositions containing the in-vivo IGF protein complex, methods of detecting ALS in body fluids, recombinant nucleic acid sequences encoding ALS, and expression vectors and host cells containing such nucleic acid sequences.

6 Claims, 8 Drawing Sheets

OTHER PUBLICATIONS

Furlanetto, Richard W., "The Somatomedin C Binding Protein: Evidence for a Heterologous Subunit Structure" *J. Clin. Endo. & Metab.* 51(1):12–19 (1980).

Guler et al., "Insulin–like growth factors I and II in healthy man. Estimations of half–lives and production rates" *Acta Endocrinologica* (Copenhagen) 121:753–758 (1989).

Hintz and Liu, "Somatomedin Plasma Binding Proteins" Growth Hormone and other Biologically Active Peptides, Pecile and Muller, Amsterdam:*Excerpta Medica* pp. 133–143 (1980).

Hintz et al., "Demonstration of Specific Plasma Protein Binding Sites for Somatomedin" *J. Clin. Endo. & Metab.* 45(5):988–995 (1977).

Lee et al., "Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors" *Mol. Endocrinol.* 2(5):404–411 (1988).

Martin & Baxter, "Antibody Against Acid–Stable Insulin-Like Growth Factor Binding Protein Detects 150,000 Mol. Wt Growth Hormone–Dependent Complex in Human Plasma" *J. Clin. Endo. & Metab.* 61(4):799–801 (1985).

Martin & Baxter, "Insulin–like Growth Factor–binding Protein from Human Plasma" *Journal of Biological Chemistry* 261(19):8754–8760 (1986).

Massague & Czech, "The Subunit Structures of Two Distinct receptors for Insulin–like Growth Factors I and II and Their Relationship to the Insulin Receptor" *Journal of Biological Chemistry* 257(9):5038–5045 (1982).

Moses et al., "Further Characterization of Growth Hormone–Dependent Somatomedin–Binding Proteins in Rat Serum and Demonstration of Somatomedin–Binding Proteins Produced by Rat Liver Cells" Endocrinology 104(2):536–546 (1979).

Pilch et al., "The Ligand Binding Subunit of the InsulinLike Growth Factor I Receptor Has Properties of a Peripheral Membrane Protein" *Biochem. & Biophys. Res. Comm.* 136(1):45–50 (1986).

White et al., "The Growth Hormone Dependence of a Somatomedin–Binding Protein in Human Serum" *J. Clin. Endo. & Metab.* 53(1):49–57 (1982).

Wilkins & D'Ercole, "Affinity–labeled Plasma Somatomedin–C/Insulinlike Growth Factor I Binding Proteins" *J. Clin. Invest.* 75:1350–1358 (1989).

Bazan et al., *Proc. Natl. Acad. Sci. USA*, 87,6934, Sep. 1990.

Anderson et al. (1990). *Gene* 90, 173.

Leong, et al., "Structure and Functional Expression of the Acid–Labile Subunit of the Insulin–Like Growth Factor–Binding Protein Complex," *Molecular Endocrinology* 6(6):870–876 (1992).

\* cited by examiner

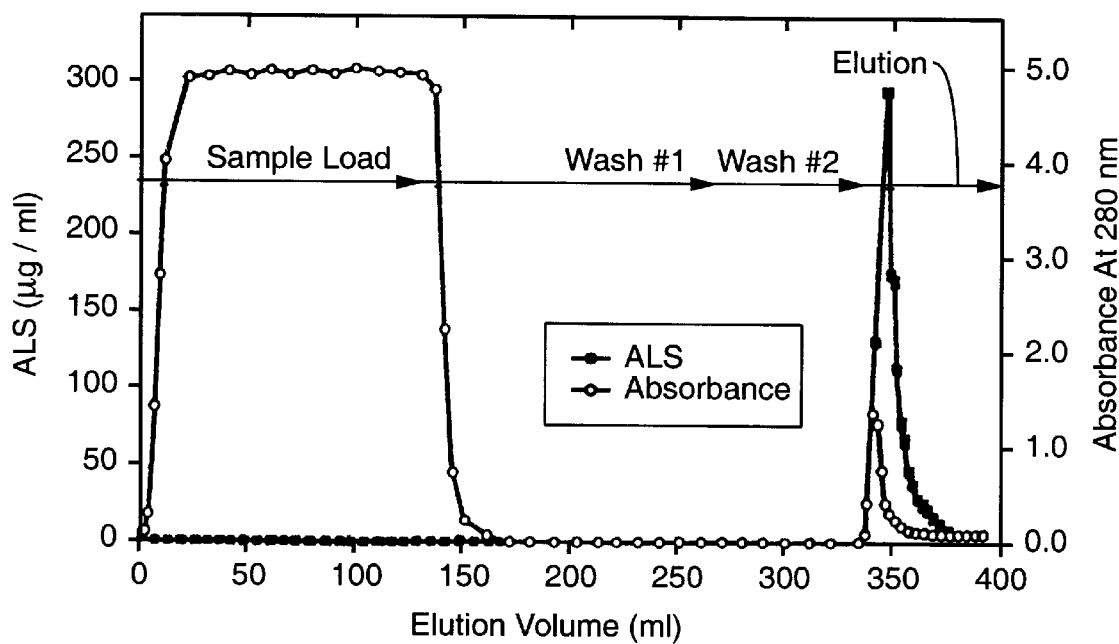
FIG._1

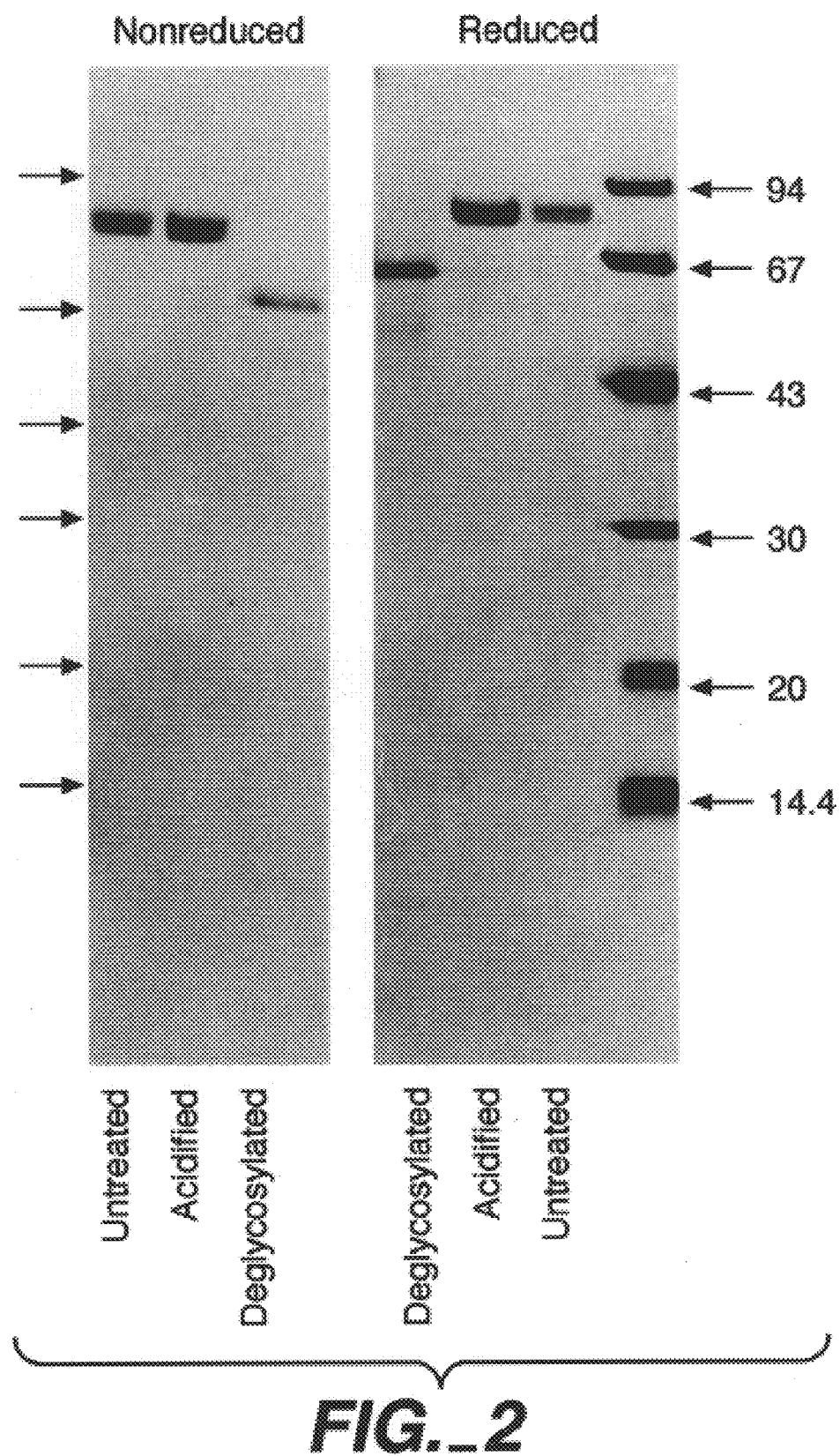
FIG._2

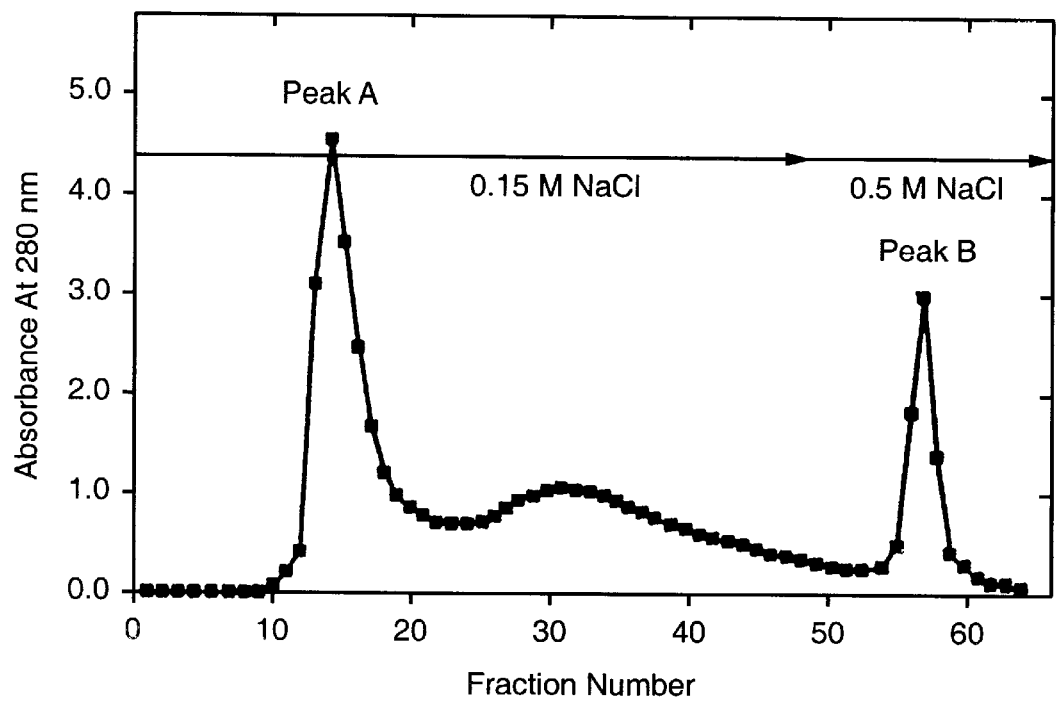
FIG._3A
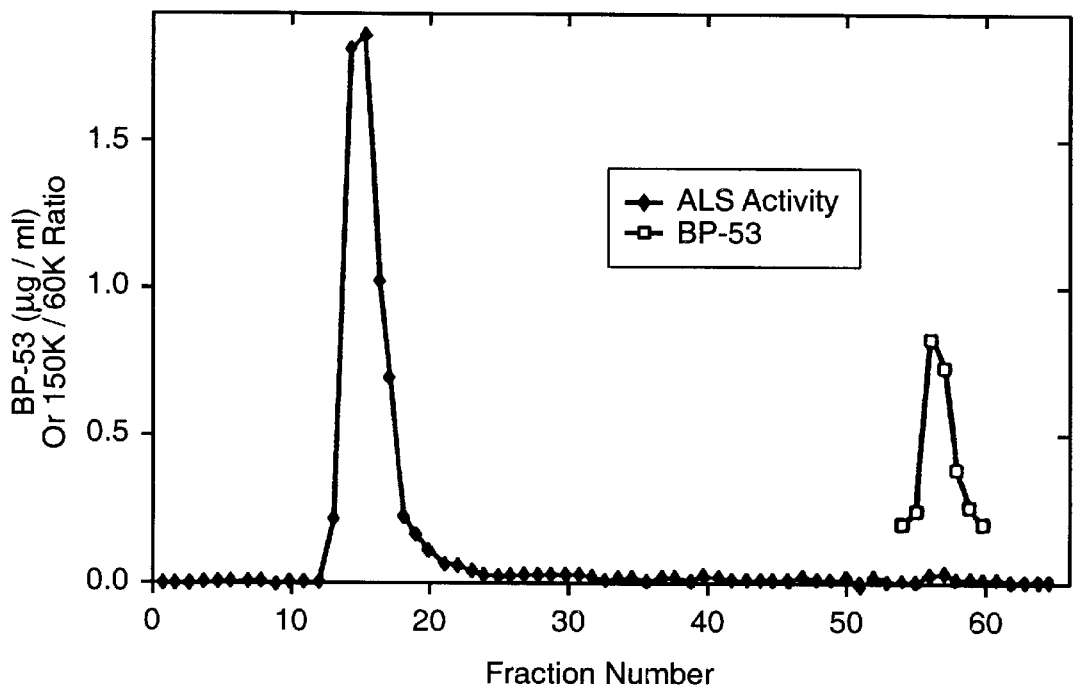
FIG._3B

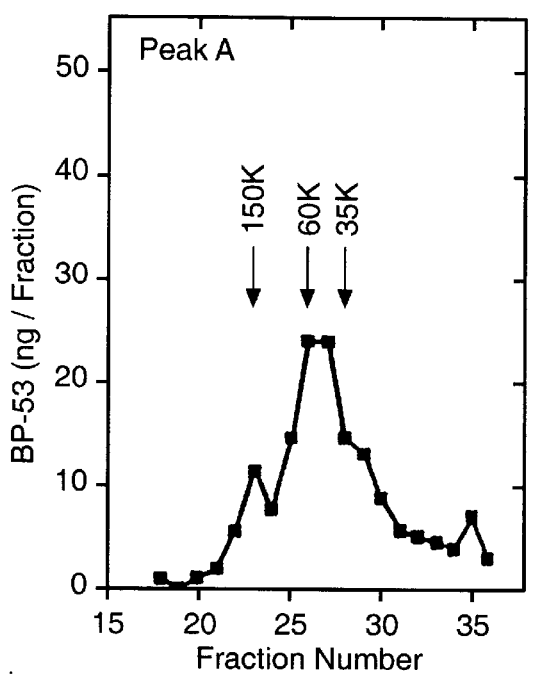
FIG._4A
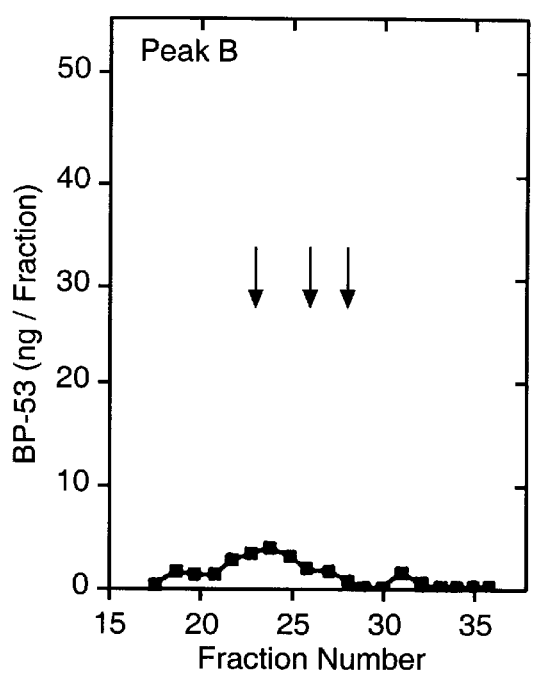
FIG._4B
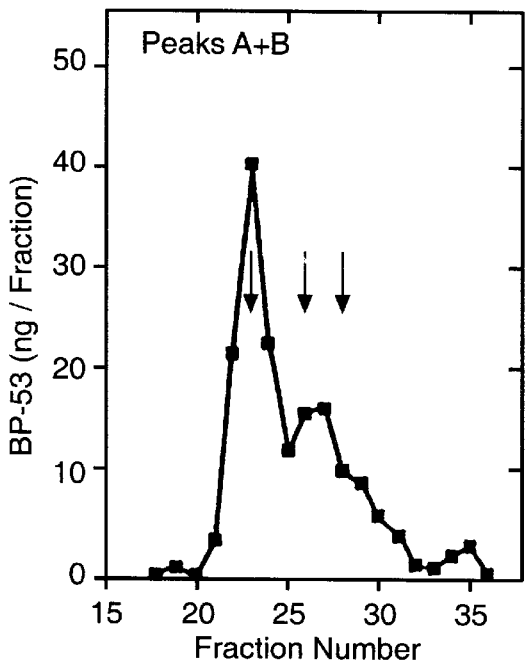
FIG._4C
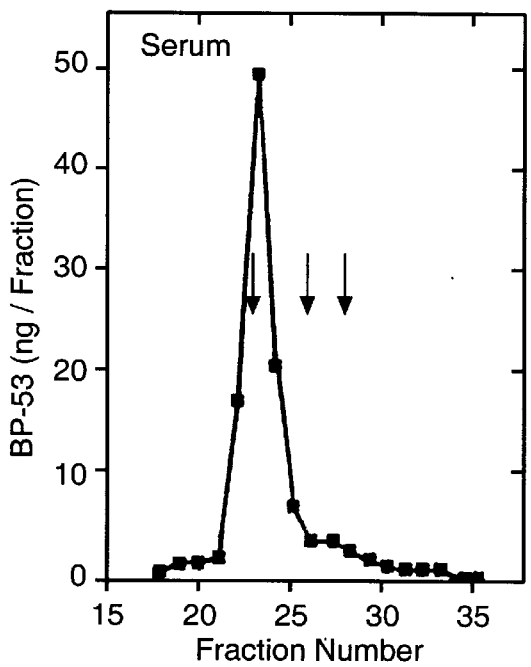
FIG._4D

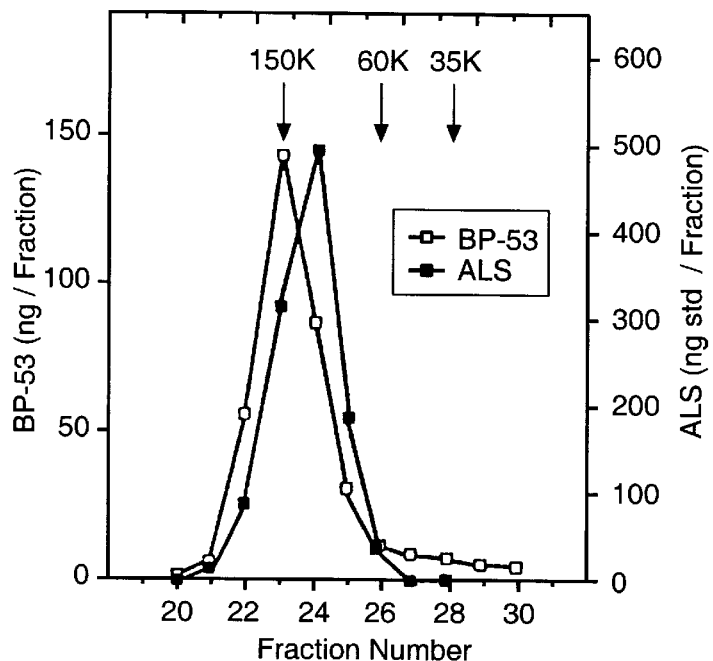
FIG._5
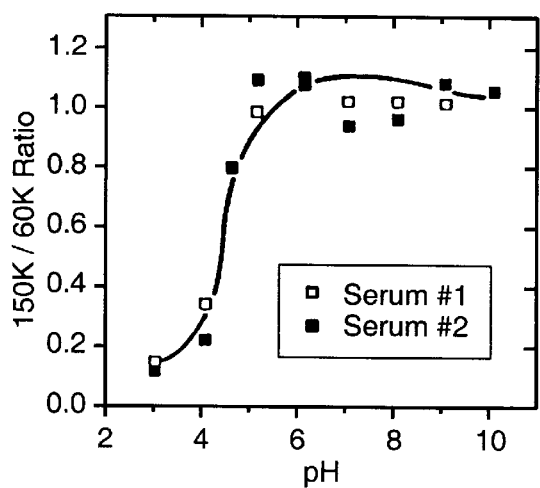
FIG._6A
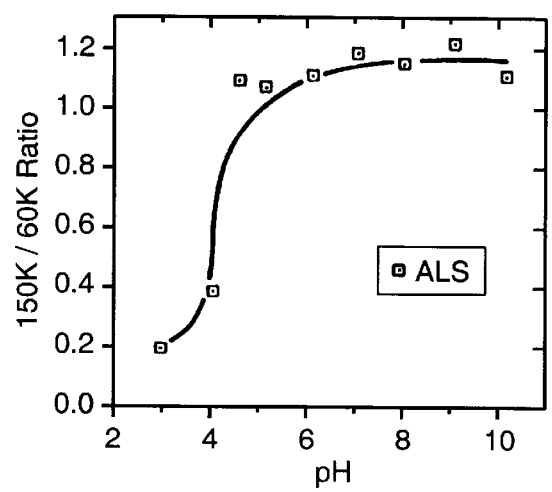
FIG._6B

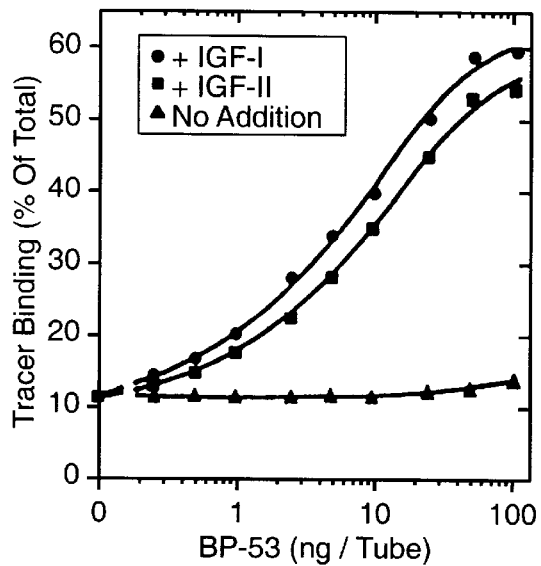
FIG._7A
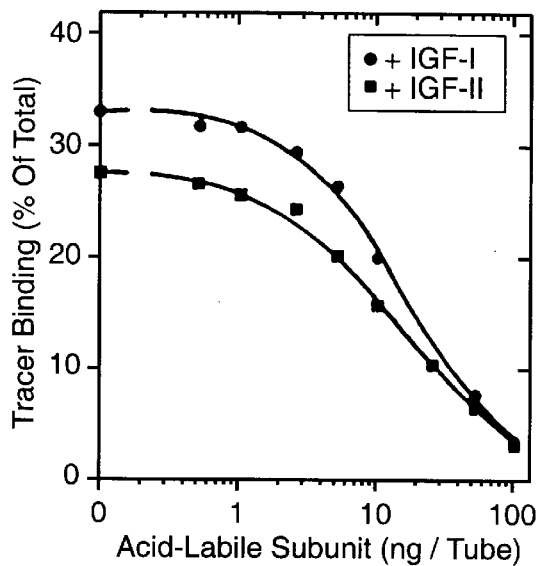
FIG._7B
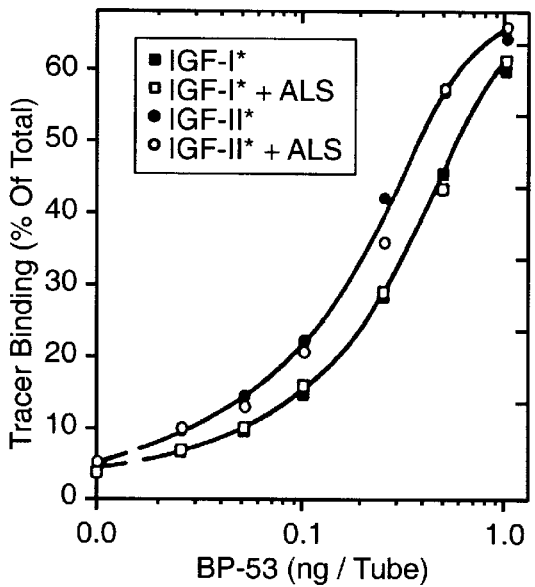
FIG._8A
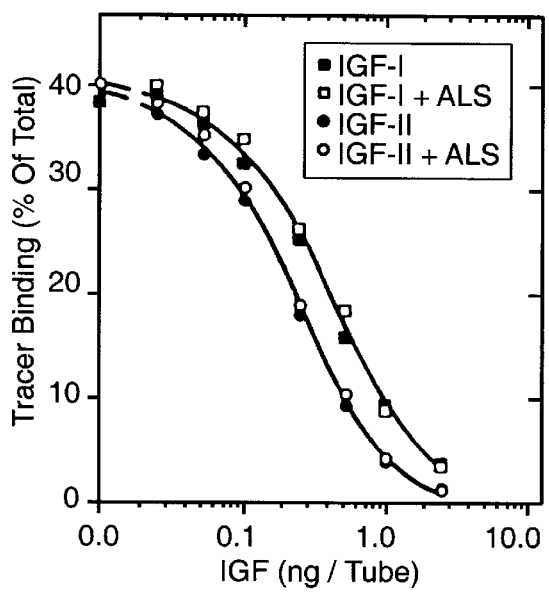
FIG._8B

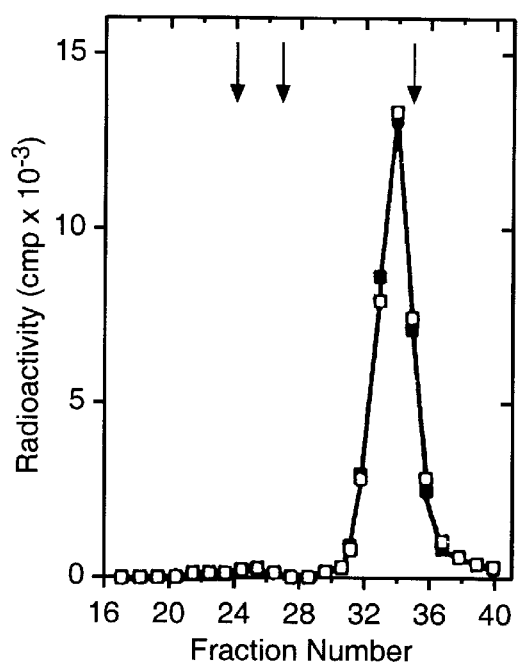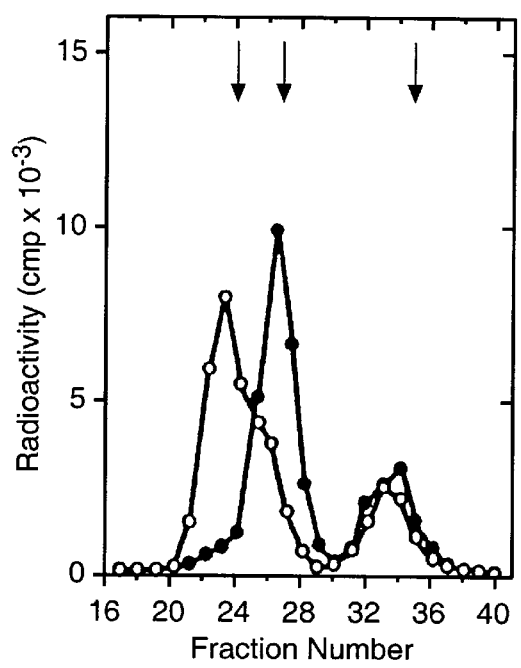
FIG._9A
FIG._9B

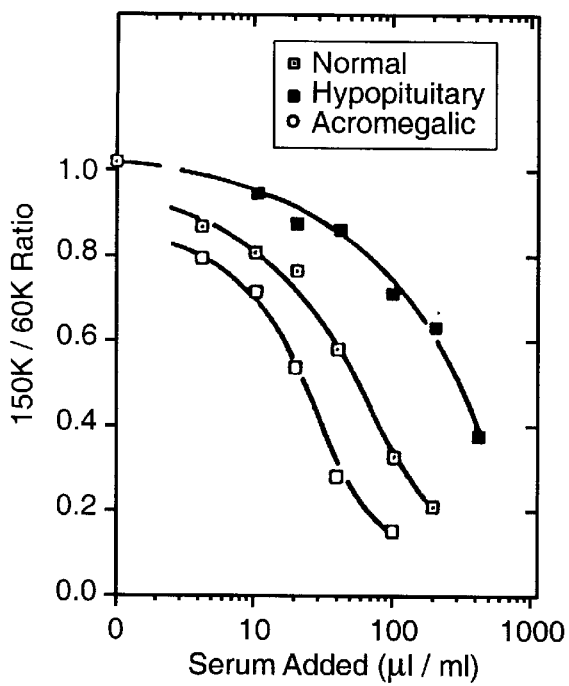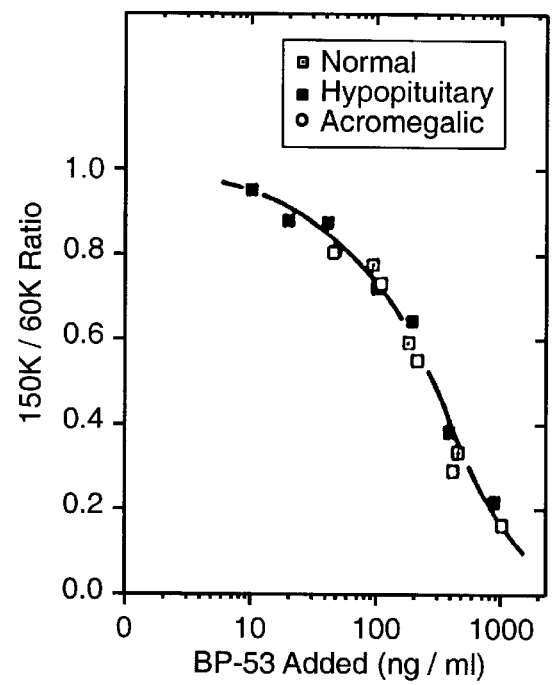
FIG._10A FIG._10B
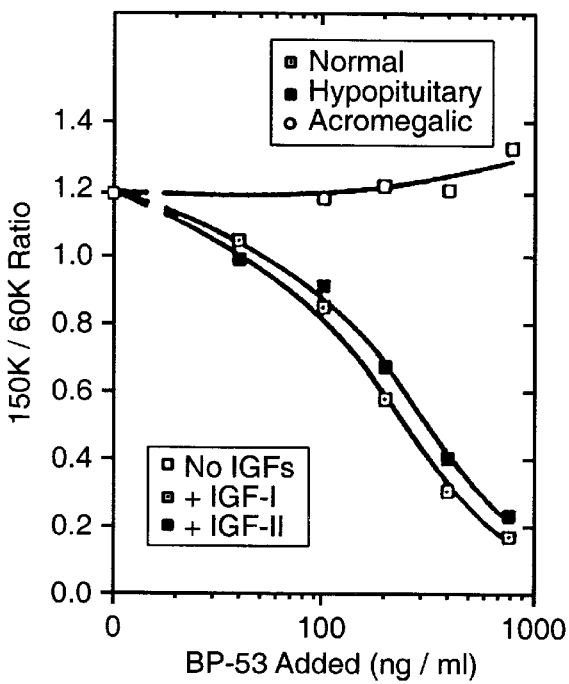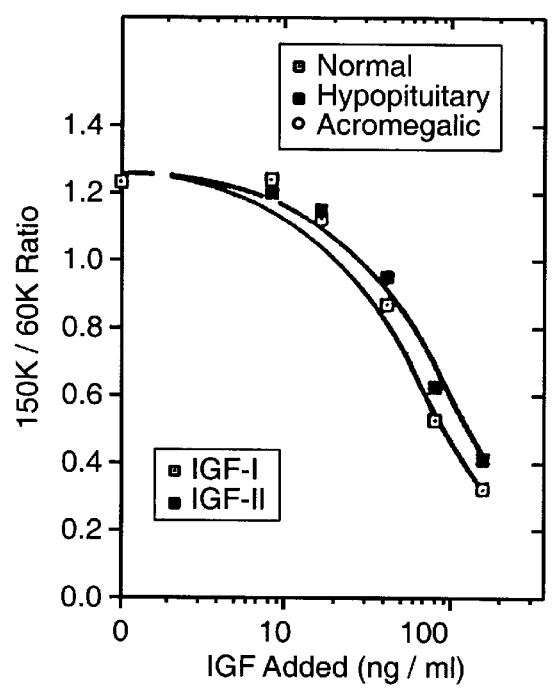
FIG._11A FIG._11B

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
       (A) LENGTH: 18 amino acids
       (B) TYPE: amino acid
       (D) TOPOLOGY: linear (xi) SEQUENCE DESCRIPTION: SEQ ID NO: 1:

Gly Asp Pro Gly Thr Pro Gly Glu Ala Glu Gly Pro Ala Cys Pro
1               5                   10                  15
Ala Ala Cys (2) INFORMATION FOR SEQ ID NO: 2:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 2:

Ala Asp Pro Gly Thr Pro Gly Glu Ala Glu Gly Pro Ala Cys Pro
1               5                   10                  15
Ala Ala Cys (2) INFORMATION FOR SEQ ID NO: 3:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 3:

Gly Asp Pro Gly Thr
1               5

(2) INFORMATION FOR SEQ ID NO: 4:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 4:

Ala Asp Pro Gly Thr
1               5

(2) INFORMATION FOR SEQ ID NO: 5:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 5:

Asp Pro Gly Thr Pro Gly
1               5

(2) INFORMATION FOR SEQ ID NO: 6:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 6:

Thr Pro Gly Glu Ala
1               5

(2) INFORMATION FOR SEQ ID NO: 7:

(i) SEQUENCE CHARACTERISTICS:
        (A) LENGTH: 5 amino acids
        (B) TYPE: amino acid (D) TOPOLOGY: linear (xi) SEQUENCE DESCRIPTION: SEQ ID NO: 7:

Gly Glu Ala Glu Gly
 1               5

(2) INFORMATION FOR SEQ ID NO: 8:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 8:

Glu Ala Glu Gly Pro Ala Cys
 1               5

(2) INFORMATION FOR SEQ ID NO: 9:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 9:

Gly Pro Ala Cys Pro
 1               5

(2) INFORMATION FOR SEQ ID NO: 10:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 10:

Ala Cys Pro Ala Ala
 1               5

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 11:

Pro Gly Thr Pro Gly Glu Ala
 1               5

(2) INFORMATION FOR SEQ ID NO: 12:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 12:

Asp Pro Gly Thr Pro Gly Glu
 1               5

(2) INFORMATION FOR SEQ ID NO: 13:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 13:

Gly Thr Pro Gly Glu Ala Glu
  1               5

(2) INFORMATION FOR SEQ ID NO: 14:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 14:

Pro Gly Glu Ala Glu Gly Pro
  1               5

(2) INFORMATION FOR SEQ ID NO: 15:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 15:

Glu Ala Glu Gly Pro Ala Cys
  1               5

(2) INFORMATION FOR SEQ ID NO: 16:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 16:

Glu Gly Pro Ala Cys Pro Ala
  1               5

(2) INFORMATION FOR SEQ ID NO: 17:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 17:

Pro Ala Cys Pro Ala Ala Cys
  1               5

(2) INFORMATION FOR SEQ ID NO: 18:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 18:

Gly Asp Pro Gly Thr Pro
  1               5

(2) INFORMATION FOR SEQ ID NO: 19:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 19:

Ala Asp Pro Gly Thr Pro
 1               5

(2) INFORMATION FOR SEQ ID NO: 20:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 20:

Thr Pro Gly Glu Ala Glu Gly
 1               5

(2) INFORMATION FOR SEQ ID NO: 21:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 21:

Gly Glu Ala Glu Gly Pro Ala
 1               5

(2) INFORMATION FOR SEQ ID NO: 22:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 22:

Ala Glu Gly Pro Ala Cys Pro
 1               5

(2) INFORMATION FOR SEQ ID NO: 23:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 23:

Gly Pro Ala Cys Pro Ala Ala
 1               5

(2) INFORMATION FOR SEQ ID NO: 24:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 24:

Gly Thr Pro Gly Glu Ala
 1               5

(2) INFORMATION FOR SEQ ID NO: 25:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 25:

-continued

```
Pro Gly Glu Ala Glu Gly
  1               5
```

(2) INFORMATION FOR SEQ ID NO: 26:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 26:

```
Glu Ala Glu Gly Pro Ala
  1               5
```

(2) INFORMATION FOR SEQ ID NO: 27:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 27:

```
Glu Gly Pro Ala Cys Pro
  1               5
```

(2) INFORMATION FOR SEQ ID NO: 28:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 28:

```
Pro Ala Cys Pro Ala Ala
  1               5
```

ACID-LABILE SUBUNIT (ALS) OF INSULIN-LIKE GROWTH FACTOR BINDING PROTEIN COMPLEX

This application is a divisional of U.S. application Ser. No. 08/459,209 filed Jun. 2, 1995 now U.S. Pat. No. 5,936,064 which is a divisional of 08/213,402 filed Mar. 14, 1994 now U.S. Pat. No. 5,561,046, which is a divisional of 07/989,962 filed Dec. 11, 1992 now U.S. Pat. No. 5,324,820, which is a continuation of 07/646,779 filed Jan. 18, 1991 now abandoned which was filed as PCT/AU/00299, Jul. 14, 1989 and claims priority to Australian Patent Applications PJ 3350/89 filed May 23, 1989 and PI 9314/88 filed Jul. 15, 1988.

FIELD OF INVENTION

This invention relates to a previously unknown and uncharacterised polypeptide, hereinafter referred to as the acid-labile sub-unit (ALS) of insulin like growth factor (IGF) binding protein complex.

Peptides of the insulin-like growth factor (IGF) family resemble insulin both in their structure and in many of their actions. The IGF family consists of two members designated IGF-I and IGF-II (IGFs). The IGFs exhibit a broad spectrum of biological activity, including anabolic insulin-like actions (e.g. stimulation of amino acid transport and glycogen synthesis), mitogenic activity and the stimulation of cell differentiation.

Human IGF-I and IGF-II have been extensively characterized, and have been found to have molecular weight of approximately 7.6 kd (IGF-I) and 7.47 Kd IGF-II).

Unlike most peptide hormones, IGFs are found in the circulation (in-vivo) and in cell culture medium in association with one or more binding proteins. The nature of the binding protein or binding proteins associated with the IGFs has been the subject of debate. Wilkins, J. R. and D'Ercole, A. J. (1985, J. Clin. Invest. 75, 1350–1358) have proposed that the in-vivo form of IGF is a complex comprising IGF in association with six identical sub-units having a molecular weight of 24 Kd to 28 Kd. In a second proposal, the in-vivo form of IGF is said to be associated with an acid-stable binding protein and an acid-labile protein(s) to generate a complex of approximately 150 Kd (Furlanetto, R. W. (1980) J.Clin. Endocrinol. Metab. 51, 12–19).

We have previously identified an acid-stable serum protein which has a single IGF-binding site per molecule, is immunologically related to the 150 Kd in-vivo form of IGF and which has an apparent molecular weight of approximately 53 Kd (Baxter, R. C., and Martin, J. L. (1986) J. Clin. Invest. 78, 1504–1512; and Martin, J. L. and Baxter, R. C. (1986) J. Biol. Chem. 261, 8754–8760). This 53 Kd IGF binding protein (BP53) appears to correspond to the acid stable binding protein proposed by Furlanetto. The 53 Kd protein is the highest molecular weight member of a family of acid-stable IGF binding proteins. Other members of this family have approximate molecular weights of 20, 34, 36, 30 and 47 Kd, and collectively fall within the definition "acid-stable IGF binding protein".

We have now surprisingly identified an acid-labile protein, which when incubated with the 53 Kd acid stable protein occupied by IGF converts it to a high molecular weight complex, corresponding to the in-vivo form of IGF.

SUMMARY OF THE INVENTION

According to one aspect of the invention there is provided the acid-labile sub-unit (ALS) of insulin like growth factor binding protein complex in biologically pure form, which preferably has the following partial N-terminal amino acid sequence:

Gly
    AspProGlyThrProGlyGluAlaGluG-
        lyProAlaCysProAlaAlaCysAla wherein the first amino acid may be Gly or Ala. (SEQ ID NOS:1 and 2, respectively).

In another aspect of the invention there is provided a composition of matter consisting essentially of the acid-labile sub-unit (ALS) of the insulin like growth factor binding complex.

In another aspect of the invention there is provided a composition, reconstituted from three polypeptide components, namely, IGF, BP-53 and ALS. The composition may be formulated to be in association with one or more pharmaceutically acceptable carriers or excipients.

In yet another aspect of the invention there is provided a process for the preparation of ALS, which comprises the steps of:

(a) applying a source of ALS to a support matrix having attached thereto IGF bound to or associated with the acid-stable IGF binding protein, whereby the ALS in the applied material binds to the acid stable binding protein and non-bound material is separated from the support matrix; and (b) selectively eluting and recovering the ALS protein from the IGF protein complex.

Preferably, ALS is prepared by a process comprising the steps of:

(a) binding IGF to a support matrix;

(b) adding the acid-stable IGF binding protein to the support matrix such that it binds to or is associated with the IGF;

(c) applying a source of ALS to the support matrix whereby the ALS in the applied material binds to the acid stable protein and non-bound material is separated from the support matrix;

(d) selectively eluting the ALS protein from the IGF protein complex; and (e) optionally further fractionating the recovered ALS by HPLC or FPLC.

According to a further aspect of the invention there is provided a method for detecting the levels of ALS in body fluids, which comprises fractionating the body fluids on a size fractionation matrix to separate free ALS from the other components of the insulin growth factor binding complex, and thereafter quantitating the levels of ALS in the fractionated sample.

In still another aspect of the invention there is provided a recombinant nucleic acid sequence encoding the acid-labile sub-unit (ALS) of insulin like growth factor. The recombinant nucleic acid sequence preferably encodes a polypeptide having the following partial N-terminal amino acid sequence:

Gly
    AspProGlyThrProGlyGluAlaGluG-
        lyProAlaCysProAlaAlaCysAla.

wherein the first amino acid is Gly or Ala. (SEQ ID NOS:1 and 2, respectively).

The invention also relates to an expression vector containing a recombinant nucleic acid sequence encoding ALS, host cells transformed with such a vector, and ALS when produced by such host cells.

In yet another aspect of the invention there are provided polypeptides comprising fragments of ALS, and nucleic acids comprising sequences encoding same, SEQ ID NOS:3 and 4, respectively which include or encode residues 1–5, SEQ ID NO:5 2–7, SEQ ID NO:6 5–9, SEQ ID NO:7 7–11, 8–14, SEQ ID NO:8 11–15, SEQ ID NO:9 13–17, SEQ ID NO:10 3–9, SEQ ID NO:11 2–8, SEQ ID NO:12 4–10, SEQ ID NO:13 6–12, SEQ ID NO:14 8–14, SEQ ID NO:15 10–16, SEQ ID NO:16 12–18, SEQ ID NO:17 1–6, SEQ ID NO:18 3–9, SEQ ID NO:19 5–11. SEQ ID NO:21 7–13, SEQ ID NO:22 9–15, SEQ ID NO:23 11–17, SEQ ID NO:24 4–9, SEQ ID NO:25 6–11, SEQ ID NO:26 8–13, SEQ ID NO:27 10–15, or SEQ ID NO:28 12–17 of ALS.

DETAILED DESCRIPTION OF THE INVENTION

The present invention relates to ALS, a polypeptide which binds to, and stabilizes in-vivo, a complex between IGF and its acid-stable binding protein BP-53. IGF can be IGF-I or IGF-II.

BP-53 is a glycoprotein, that is, one or more carbohydrate chains are associated with the BP-53 polypeptide sequence. Where mention is made of the acid-stable IGF binding protein or BP-53, it is to be understood to refer to an acid-stable protein capable of binding to insulin like growth factor, and capable of forming a complex with ALS and IGF. As long as the acid-stable IGF binding protein or BP-53 satisfies these functions, it may be non-glycosylated, partly glycosylated, modified by way of amino acid deletions or substitutions or insertions, and may have a molecular weight of 20, 30, 34, 36, 47 and 53 Kd. The precise molecular weight of this component is generally unimportant.

In accordance with the present invention and using the methods disclosed herein, said ALS is biologically pure. By biologically pure is meant a composition comprising at least 65% by weight of ALS and preferably at least 75% by weight. Even more preferably, the composition comprises at least 80% ALS. Accordingly, the composition may contain homogeneous ALS. In this specification, the term "biologically pure" has the same meaning as "essentially or substantially pure".

Where this invention relates to a composition of matter consisting essentially of ALS, the term "composition of matter" is to be considered in a broad context. The composition of matter may be ALS itself, or ALS in association with one or more pharmaceutically or veterinarially acceptable carriers or excipients. Suitable carriers may include water, glycerol, sucrose, buffers or other proteins such as albumin, etc. The term "consisting essentially of" has the same meaning as "biologically pure" discussed above.

By binding to IGF is meant the ability of ALS to bind to complexes formed when IGF is bound or associated with an acid-stable component, BP-53.

ALS is a glycoprotein, that is, one or more carbohydrate chains are associated with the ALS polypeptide sequence. This invention extends to ALS in its fully glycosylated, partially glycosylated or non-glycosylated forms, which may be readily prepared according to methods well known in the art. For example, ALS prepared according to the methods disclosed herein may be reacted with enzymes, such as endoglycosidases, to remove N-linked carbohydrate either partially or totally. O-linked carbohydrate may similarly be removed by well known methods.

As mentioned previously, ALS preferably has the following partial N-terminal amino aoid sequence:

Gly
    AspProGlyThrProGlyGluAlaGlu-
    lyProAlaCysProAlaAlaCysAla where the first amino acid may be Gly or Ala. (SEQ ID NOS:1 and 2, respectively).

It is to be understood, however, that the ALS of the present invention is not restricted to possessing the above N-terminal amino acid sequence. Rather, ALS is functionally defined as an acid-labile polypeptide which is capable of binding to or associating with complexes formed when IGF is bound or associated with the acid stable binding protein BP-53 defined above. The definition ALS extends to encompass synthetic and naturally occurring amino acid substitutions, deletions and/or insertions to the natural sequence of ALS, as will be readily apparent to the skilled artisan. For example, genetic engineering means can be readily employed using known techniques to substitute, delete and/or insert amino acids.

Generally, and in no way limiting the invention, ALS may be characterized in that it:
(i) is acid-labile, that is, it is unstable at a pH less than 4,
(ii) binds to an acid stable IGF binding protein which is occupied by IGF, and
(iii) has an approximate molecular weight between 80 Kd and 115 Kd as determined by SDS-PAGE.

ALS referred to herein is human ALS. Animal ALS, which is capable of forming a complex with animal IGF, is also to be understood to fall within the scope of the term ALS.

ALS is contemplated herein to be useful in the preparation of the physiological IGF complex which comprises IGF, BP-53 and ALS. Such a complex may be useful in wound-healing and associated therapies concerned with re-growth of tissue, such as connective tissue, skin and bone; in promoting body growth in humans and animals; and in stimulating other growth-related processes. The ALS protein also confers a considerable increase in the half-life of IGF in-vivo. The half-life of IGF per se, unaccompanied by binding proteins, is only a few minutes. When IGF is in the form of a complex with the acid-stable IGF binding protein, and the ALS protein, its half-life is increased to several hours, thus increasing the bio-availability of IGF with its attendant therapeutic actions. Furthermore, pure ALS may be used to raise specific monoclonal or polyclonal antibodies, in order to establish a radioimmunoassay or other assay for ALS. Measurement of ALS in human serum may be useful in diagnosing the growth hormone status of patients with growth disorders.

The IGF binding protein complex formed by. admixing ALS, IGF and the acid stable protein BP-53, where each component is preferably in biologically pure form, may be formulated with suitable pharmaceutically and/or therapeutically or veterinarially acceptable carriers and used for example, in growth promotion or wound treatment in human and non-human animals. Examples of pharmaceutically acceptable carriers include physiological saline solutions, serum albumin, or plasma preparations. Depending on the mode of intended administration, compositions of the IGF binding protein complex may be in the form of solid, semi-solid or liquid dosage preparations, such as for example, tablets, pills, powders, capsules, liquids, suspensions or the like. Alternatively, the IGF binding protein complex may be incorporated into a slow release implant, such as osmotic pumps for the release of material over an extended time period.

The amount of the IGF binding protein complex administered to human patients or animals for therapeutic purposes will depend upon the particular disorder or disease to be treated, the manner of administration, and the judgement of the prescribing physician or veterinarian.

ALS may be purified from human serum or plasma, or plasma fractions such as Cohn Fraction IV. Purification from whole serum is preferred, this being the most economical and plentiful source of material and giving the highest yield. Purification of ALS exploits the physiological interaction between IGF, BP-53 and ALS. ALS is recovered from human serum by passing the serum through a support matrix having IGF-BP-53 bound or associated therewith. Reference to association means a non-covalent interaction, such as electrostatic attraction or hydrophobic interactions. ALS bound to the IGF-BP-53 affinity matrix may then be eluted by disrupting the interaction between ALS and the affinity matrix, for example by increasing ionic strength (e.g. at least 0.3M NaCl, or other equivalent salt) or conditions of alkaline pH (above pH 8).

A source of ALS such as whole plasma or Cohn Fraction IV thereof may be fractionated on an ionic 30resin to enrich the amount of ALS prior to application to the affinity matrix. A cation exchange resin is preferred. Optionally, ALS purified by affinity chromatography is subjected to a further purification step such as HPLC or FPLC (Trademark, Pharmacia). The HPLC step may, for example, be conducted using a reverse phase matrix, a gel permeation matrix or an ionic matrix.

Where this invention is concerned with antibodies which are capable of binding to ALS, the antibodies may be monoclonal or polyclonal. Such antibodies may be used to measure ALS levels in serum, and may form part of a diagnostic kit for testing growth related disorders. Antibodies against ALS may be prepared by immunizing animals (for example; mice, rats, goats, rabbits, horses, sheep or even man) with purified ALS according to conventional procedures (Goding, J. W. (1986) Monoclonal Antibodies: Principles and Practices, 2nd Edition, Academic Press). Serum proteins may, for example, be attached to a support matrix, and incubated with anti-ALS antibodies which may be labelled with reporter groups (for example, fluorescent groups, enzymes or colloidal groups) to detect ALS. Alternatively, non-labelled anti-ALS antibodies bound to ALS may be reacted with suitable agents (such as antibodies directed against anti-ALS antibodies or anti-immunoglobulin antibodies) to detect antibody binding, and thus quantitate ALS levels.

Where this invention relates to a recombinant nucleic acid molecule, said molecule is defined herein to be DNA or RNA, encoding ALS or parts thereof. In one embodiment, the recombinant nucleic acid molecule is complementary DNA (cDNA) encoding mammalian and preferably, human ALS, or parts thereof including any base deletion, insertion or substitution or any other alteration with respect to nucleotide sequence or chemical composition (e.g. methylation). ALS encoded by cDNA is herein referred to as recombinant ALS.

A recombinant nucleic acid which exhibits at least 60% sequence homology or more preferably 80 to 99% homology with nucleic acid (cDNA, DNA, RNA) encoding ALS, or which encodes a protein having the biological activity of ALS, is to be regarded as nucleic acid encoding ALS.

Methods considered useful in obtaining recombinant ALS cDNA are contained in Maniatis et. al., 1982, in *Molecular Cloning: A Laboratory Manual*, Cold Spring Harbour Laboratory, New York. pp 1–545. Briefly, polyadenylated MRNA is obtained from an appropriate cell or tissue source, such as liver. Optionally, MRNA is fractionated on agarose gels, or gradient centrifugation, and translated and assayed for ALS, such as, for example, by immunoprecipitation. Enriched or unenriched mRNA is used as a template for cDNA synthesis. Libraries of cDNA clones are constructed in the Pstl site of a vector such as pBR 322 (using homopolymeric tailing) or other vectors; or are constructed by ligating linkers (such as Eco Rl linkers) onto the ends of cDNA, which is then cloned into a vector having sites complementary to said linkers. Specific cDNA molecules in a vector in a library are then selected using specific oligonucleotides based on the aforementioned N-terminal amino acid sequence of ALS. Alternatively, commercially available human lambda libraries may be screened with oligonucleotides. In an alternative approach, the cDNA may be inserted into an expression vector such as lambda gt 11, with selection based on the reaction of expressed protein with a specific antibody raised against purified ALS. In any event, once identified, cDNA molecules encoding all or part of ALS are then ligated into expression vectors. Additional genetic manipulation is routinely carried out to maximise expression of the cDNA in the particular host employed.

Accordingly, ALS is synthesized in vivo by inserting said cDNA sequence into an expression vector, transforming the resulting recombinant molecule into a suitable host and then culturing or growing the transformed host under conditions requisite for the synthesis of the molecule. The recombinant molecule defined herein should comprise a nucleic acid sequence encoding a desired polypeptide inserted downstream of a promoter functional in the desired host, a eukaryotic or prokaryotic replicon and a selectable marker such as one resistant to an antibiotic. The recombinant molecule may also require a signal sequence to facilitate transport of the synthesized polypeptide to the extracellular environment. Alternatively, the polypeptide may be retrieved by first lysing the host cell by a variety of techniques such as sonication, pressure disintegration or detergent treatment. Hosts contemplated in accordance with the present invention can be selected from the group comprising prokaryotes (e.g., *Escherichia coli*, Bacillus sp., Pseudomonas sp.) and eukaryotes (e.g., mammalian cells, yeast and fungal cultures, insect cells and plant cultures). The skilled person will also recognize that a given amino acid sequence can undergo deletions, substitutions and additions of nucleotides or triplet nucleotides (codons). Such variations are all considered within the scope of the present invention. Additionally, depending on the host expressing recombinant ALS, said ALS may or may not be glycosylated. Generally, eukaryotic cells, for example mammalian cells and the like, will glycosylate the recombinant ALS. Prokaryotic cells, for example, bacteria such as *Escherichia coli* and the like, will not glycosylate the recombinant ALS. Both glycosylated and non-glycosylated ALS are encompassed by the present invention, as has been previously mentioned.

| ABBREVIATIONS | |
|---|---|
| IGF | insulin-like growth factor |
| SDS-PAGE | sodium dodecylsulphate polyacrylamide gel electrophoresis |
| Kd or K | kilodaltons |
| GH | growth hormone |

The following drawings and Examples are illustrative of, but in no way limiting, on the present invention.

BRIEF DESCRIPTION OF THE FIGURES

FIG. 1: Affinity chromatography of ALS. A 132-ml pool of fractions partially purified by DEAE-Sephadex chromatography was loaded at 0.13 ml/min onto a 1×15 cm affinity column containing a mixture of IGF-I and IGF-II covalently bound to agarose, to which BP-53 had been noncovalently adsorbed. The column was washed with 150 ml of 50 mM Na phosphate, pH 6.5 (Wash #1) and 50 ml of 5 mM Na phosphate, 50 mM NaCl, pH 6.5 (wash #2), at 1 ml/min. ALS was eluted by applying 50 mM Tris-HCl, 0.3 M NaCl, pH 8.5, at 0.5 ml/min.

FIG. 2: SDS-polyacrylamide gel electrophoresis of purified ALS. Left panel: Untreated, acidified, and N-glycanase-treated samples (15 µg/lane) run under nonreducing conditions. Right panel: the same samples in reverse order, run under reducing conditions. Gels were stained with Coomassie blue. The molecular masses (in kDa) of standard proteins, shown in the right hand lane for the reduced gel, are also indicated by arrows on the left for standards run on the nonreduced gel.

FIG. 3 shows fractionation of human serum on a column of DEAE-Sephadex A-50. One milliliter dialyzed serum was loaded onto a 1×17.5 cm. gel bed, the column was washed with 35 mL 0.05 mol/L Tris-HCl. pH 8.2 and elution commenced with 50 mL of the same buffer containing 0.15 mol/L NaCl. Elution was then continued with the same buffer containing 0.6 mol/L NaCl. Fractions of 1 mL were collected and assayed for absorbance at 280 nm and BP-53 by RIA. ALS was determined on 20-µL aliquots of peak B fractions by the routine assay method;

FIG. 4 depicts the generation of the 150K complex from DEAE-Sephadex-fractionated serum. Peak A and B pools, as in FIG. 3, were prepared by DEAE-Sephadex chromatography of 10 mL serum, then fractionated by Superose-12 chromatography. The samples, injected in a volume of. 200 µL each, were peak A (a: 100 µL), peak B (b: 100 µL) peaks A and B (c: 100 µl each), mixed and incubated for 1 h at 22° C. before loading, and whole serum (d: 33 µL). BP-53 immunoreactivity was measured on 50 µL of each 0.5 mL fraction. Arrows indicate 150K, 60K and 35K markers;

FIG. 5 shows the comparison of BP-53 immunoreactivity and ALS activity, as indicated in serum fractionated on Superose-12. Each fraction was 0.5 mL. The arrows indicate 150K, 60K and 35K markers. Note that the method used to detect ALS protein only detects protein not present as the 150K complex;

FIG. 6 depicts acid lability of ALS activity. Samples of normal serum (a) or partially pure ALS (b) were diluted in ALS assay buffer and adjusted to the pH values shown with 1 mol/L HCl or NaOH. After 30 min at 22° C., the samples were reneutralized and assayed for ALS activity in the routine assay (10 µL serum or 600 ng ALS preparation/ incubation);

FIG. 7 shows the effect of IGFs on ALS binding to BP-53. Left panel: Increasing concentrations of BP-53 were incubated in a 300 µL reaction volume with [$^{125}$I]-labeled ALS tracer in the presence or absence of IGF-I or IGF-II (50 ng/tube), as indicated. Right panel: Competitive binding study in which 10 ng BP-53 plus 10 ng IGF-I or IGF-II was incubated in 300 µl with ALS tracer and increasing concentrations of unlabelled ALS. Tracer bound to BP-53 was immunoprecipitated with anti-BP-53 antiserum R-7.

FIG. 8 shows the effect of ALS on IGF binding to BP-53. Left panel: Increasing concentrations of BP-53 were incubated in a 300 µl reaction volume with [$^{125}$I]-labeled IGF-I or IGF-II tracer (IGF-I* or IGF-II*) in the presence or absence of ALS (100 ng/tube), as indicated. Right panel: Competitive binding study in which 0.25 ng BP-53, in the presence or absence of 100 ng ALS, was incubated in 300 µl with IGF-II tracer and increasing concentrations of unlabelled IGF-I or IGF-II, as indicated. Tracer bound to BP-53 was immunoprecipitated with anti-BP-53 antiserum R-7.

FIG. 9 shows the effect of BP-53 and ALS on the gel chromatographic profile of [$^{125}$I]-labeled IGF-II tracer. Samples of 200 µl containing 50,000 cpm of IGF-II tracer, preincubated 2h at 22° C. in the presence or absence of BP-53 (1 ng/200 µl) or ALS (100 ng/200 µl), were chromatographed on a Superose-12 high performance chromatography column in 50 mM Na phosphate, 0.15 M NaCl, 0.02% Na azide, 0.1% bovine albumin, pH 6.5. Fractions of 0.5 ml were collected at 1 ml/min, and the radioactivity in each fraction determined. On each panel the three arrows indicate, from left to right, molecular weight markers of 150 kDa, 60 kDa and 7.5 kDa. Left panel: solid symbols, IGF-II tracer; open symbols, tracer plus ALS. Right panel: solid symbols, tracer plus BP-53; open symbols, tracer plus BP-53 plus ALS.

FIG. 10 shows competition by increasing concentrations of acidified-neutralized human serum from normal, hypopituitary or acromegalic subjects in the routine ALS assay, in which 600 ng of partially purified ALS/250 µL incubation medium (i.e. 2.4 µg/mL) gave a 150K/60K ratio of approximately 1 in the absence of added serum. The serum concentration is expressed in terms of volume (a) or in terms of the immunoreactive BP-53 content (b). The acidified-neutralized serum samples illustrated contained 4.49 µg/mL (normal), 0.93 µg/mL (hypopituitary), or 10.49 µg/mL (acromegalic) BP 53 by RIA; and FIG. 11 depicts competition by pure BP-53 in the routine ALS assay, (a) the effect of increasing BP-53 concentrations after preincubation without IGFs or with a 3.5-fold molar excess of pure human IGF-I or IGF-II, as indicated. Panel (b), shows the effect of a fixed BP-53 concentration (0.8 µg/mL) preincubated with increasing concentrations of IGF-I or IGF-II.

EXAMPLES

Example 1

Materials

Fresh human serum for ALS preparation was obtained from laboratory volunteers. Cohn Fraction IV of human plasma, provided by Commonwealth Serum Laboratories, Melbourne, Australia, was used as starting material to prepare human IGF-I and IGF-II, and the IGF-binding protein BP-53. DEAE-Sephadex A-50, SP-Sephadex C-25, electrophoresis standards, and the Superose 12 HR 10/30 column were obtained from Pharmacia, Sydney; Affi-Gel 10 and Affi-Gel 15 were purchased from Bio-Rad; and the Poly-WAX LP (polyethleneimine) anion exchange HPLC column (200×4.6 mm) was from PolyLC, Columbia, Md. All other reagents were at least analytical grade.

Human IGF-I and IGF-II were isolated and iodinated as previously described (Baxter, R.C., and De Mellow, J. S. M. (1986) Clin. Endocrinol. 24, 267–278; and Baxter, R. C., and Brown, A. S. (1982) Clin. Chem. 28, 485), and IGF-I tracer was further purified by hydrophobic interaction chromatography (Baxter, R. C., and Brown, A. S. (1982) Clin. Chem. 28, 485). The 53K IGF-binding protein BP-53 was purified from Cohn fraction IV as previously described (Martin, J. L., and Baxter, R. C. (1986) J. Biol. Chem. 261, 8754–8760), and a covalent complex with [$^{125}$I]IGF-I, cross-linked using disuccinimidyl suberate, was prepared and purified by gel chromatography according to the method of Baxter, R. C., and Martin, J. L. (1986) J. clin. Invest. 78, 1504–1512. A 28K IGF-binding protein BP-28 was purified from human amniotic fluid by affinity chromatography and reverse phase high pressure liquid chromatograph according to Baxter, R. C., Martin, J. L. and Wood, N. H. (1987), J. Clin. Endocrinol. Metab. 65, 423–431.

ALS Iodination and Radioimmunoassay:

[$^{125}$I]-labeled ALS was prepared by reacting 5 μg ALS in 50 μL M Na phosphate buffer, pH 7.4, for 20 sec with 1 mCi Na$^{125}$I and 10 μg chloramine-T, then terminating the reaction with 50 μg Na metabisulfite. An antiserum against ALS was raised by immunizing a rabbit over a 7-week period with 4 doses of approximately 100 μg purified ALS. Radioimmunoassay incubations in 0.5 ml final volume contained antiserum at 1:50,000 final dilution, [$^{125}$I]-labeled ALS (approx. 10,000 cpm per tube), and ALS in the range 0.5–100 ng/tube. After a 16 h incubation at 22° C., bound and free tracer were separated by centrifugation following the addition of goat anti-rabbit immunoglobulin (2 μl), carrier normal rabbit serum (0.5 μl), and, after 30 min, 1 ml 6% polyethylene glycol in 0.15 N NaCl.

Assay for ALS:

The routine assay for ALS activity was developed, based on the conversion of a covalent BP-53-IGF-I complex of approximately 60K to 150K form in the presence of ALS.

Samples to be tested for ALS activity were diluted to 200 μL in buffer containing 50 mmol/L sodium phosphate, 0.15 mol/L NaCl, and 0.2 g/L sodium azide, pH 6.5, with 10 g/L bovine albumin. Cross-linked BP-53-IGF-I tracer (~80,000 cpm; 4 ng) was added in 50 μL of the same buffer. After 25–30 min. of incubation at 22° C., 200 μL of the mixture was applied using a V-7 injector valve (Pharmacia) to a Superose-12 gel permeation column eluting at 1.0 mL/min (~2 megapascal pressure) in assay buffer without albumin. The column was calibrated with rabbit immunoglobulin G (Pentex; ~150K), which eluted mainly in fractions 22~24, peaking in fraction 23; BP-53-IGF-I tracer (~60K), which eluted mainly in fractions 25–27, peaking in fraction 26; IGF-I tracer bound to BP-28 (~35K, peaking in fraction 28); and IGF-I tracer (7.5K, peaking in fraction 33). Plotted as log (molecular mass) vs. elution volume, these four markers yielded a linear calibration curve (not shown). As a quantitative index of ALS activity (i.e. the degree of conversion of BP-53 to the 150K complex), the total radioactivity in fractions 22–24 was divided by that in fractions 25–27 to give a 150K/60K ratio. The values of this ratio typically varied between 0.1 and 2.0. The coefficient of variation of the 150K/60K ratio, based on analysis of variance of eight duplicate measurements covering a wide range of values, was 3.2%. Because each chromatography run took 30 min., and the precision of the assay was high, each determination was generally performed singly within each experiment.

In the absence of ALS, the radioactivity was found predominantly in fractions 25–27, corresponding to a molecular mass of 60K, typically giving a 150K/60K ratio of 0.10 or lower. Increasing concentrations of ALS in the preincubation caused increasing conversion of the 60K tracer to the 150K form (fractions 22–24), giving higher values for the 150K/60K ratio. Both IGF-I and IGF-II tracers, preincubated with pure BP-53 but not covalently cross-linked, could also be converted to 150K by incubation with ALS. Other IGF acid-stable binding proteins structurally related to BP-53 but of smaller size (such as those of 20, 24, 26, 30 and 47K) also participate in this reaction to form corresponding smaller complexes. Cross-linked BP-53-IGF-II tracer was not tested. A dose-response curve using the purified ALS preparation produced according to Example 2 was constructed using cross-linked BP-53-IGF-I tracer. A highly reproducible sigmoidal semilog plot was obtained, which could be used as a standard curve for quantitating the ALS in unknown samples (for example during purification). A similar result is obtained if the tracer complexed to ALS is precipitated with an anti-ALS antiserum instead of being fractionated on a Superose-12 column.

Example 2

Purification of ALS:

Fresh human serum or Cohn Factor IV paste of human plasma were used as a source of ALS. Fresh human serum (100–130 ml) was dialyzed against 2×50 vol of 0.05 M Tris-HCl pH 8.2 at 2° C., then loaded onto a column of DEAE Sephadex A-50 (5×23 cm) equilibrated with dialysis buffer at 22° C. The column was washed with 2 liters of dialysis buffer, then with 2–2.5 liters of the same buffer containing 0.15 M NaCl. This step removed all of the immunoreactive BP-53 from the column. ALS was eluted by applying 1 liter of 0.05 M Tris-HCl, 0.6 M NaCl, pH 8.2, pumping at 1 ml/min. Fractions of 10 ml were collected and assayed for ALS activity and absorbance at 280 nm. Active fractions were combined (approximately 140 ml total) and dialyzed at 2° C. against 5 liters of 50 mM sodium phosphate, 0.02% Na azide, pH 6.5.

Where Cohn Factor IV is the source of ALS, the frozen paste (600 g) was broken into small pieces and extracted for 16 h at 2° C. by stirring with 3 liters 50 mM Tris-HCl, 0.15 M NaCl, 0.02% sodium azide, pH 8.2. The mixture was centrifuged 30 min at 12000 rpm in the GSA rotor of a Sorvall RC5C centrifuge, yielding a turbid green-brown supernatant fraction (2.8 liter). This was divided into two equal portions and loaded by gravity feed onto two columns of DEAE Sephadex A-50 (5×22 cm) equilibrated with extraction buffer, and each column was washed with 2 liters of buffer. At this stage a predominant blue-green band was concentrated in the upper half of the column. Sometimes this band started to migrate through the column during the washing step; in these cases the washing volume was decreased to 1 liter. ALS was eluted from the column by a linear 0.15–0.35 M NaCl gradient in 50 mM Tris-HCl, 0.02% sodium azide, pH 8.2 (2 liter total volume). Fractions of 10 ml were collected and assayed for ALS activity and absorbance at 280 nm (or protein by a Biuret method). Active fractions from the two parallel columns were combined (approximately 1 liter total), diluted two-fold with 50 mM sodium phosphate pH 6.5, and the pH adjusted to 6.5 by slow addition of 1 M HCl. Since the active fractions corresponded closely with the blue-green protein in the eluted fractions, this provided a convenient visual marker for the progress of the activity through the ion-exchange procedure.

The ALS containing fractions obtained from plasma or Cohn Factor IV, as detailed above, were applied to either one of two IGF affinity columns: (1) Affi-Gel column (1×12 cm) to which 3 mg IGF-II had been coupled exactly as previously described (Martin, J. L., and Baxter, R. C. (1986) J. Biol. Chem. 261, 8754–8760), or (2) Affi-Gel 10 column (1×15 cm) to which a mixture containing approximately 5 mg IGF-I and 2 mg IGF-II had been coupled by the same procedure. The affinity column was loaded with BP-53, prepared exactly as previously described (Martin, J. L., and Baxter, R. C. (1986) Supra). Briefly, 600 g Cohn paste was homogenized with 5 vol of 2 M acetic acid, 75 mM NaCl, the mixture was centrifuged, and the supernatant was depleted of endogenous IGFs by stirring 2–3 days with approximately 400 ml packed volume of SP-Sephadex C-25 which had been equilibrated in the homogenizing buffer at pH 3.0. The mixture was centrifuged to remove the gel, and the supernatant was adjusted to pH 6.5 in two steps, as previously described (Martin, J. L., and Baxter, R. C. (1986)

Supra). The pH 6.5 supernatant was then pumped at approximately 0.5 ml/min onto the affinity column, and the column was washed at 1–2 ml/min with 250 ml of 50 mM Na phosphate, 0.5 M NaCl, pH 6.5, and 100 ml of 50 mM Na phosphate, pH 6.5.

ALS containing fractions from DEAE-Sephadex chromatography were pumped at 0.1–0.15 ml/min onto the IGF affinity column loaded with BP-53. This typically resulted in the retention of over 90% of the ALS activity. The column was washed at 1 ml/min with 150 ml of 50 mM Na phosphate, pH 6.5, and 50 ml mM NaCl, 5 mM Na phosphate pH 6.5, to lower the buffering capacity of the column. ALS was eluted by applying 50 mM Tris-HCl, 0.3 M NaCl, pH 8.5 to the column at 0.5 ml/min. This is illustrated in FIG. 1 which shows a plot of elution volume from the affinity column against ALS ($\mu$g/ml) and absorbance at 280 nm. Fractions of 2 ml were collected in siliconized glass tubes and assayed for ALS activity.

SDS-PAGE (10%) of the immunopurified ALS, under reducing conditions, yielded a doublet of closely associated bands with an approximate molecular weight of 90K. The doublet may be due to varying glycosylation of ALS. No other bands were present, this indicating that the ALS was homogeneous.

As an optional final purification step affinity-purified ALS was fractionated by high-performance anion exchange chromatography. Sample loads of 0.5 ml per run were applied to a PolyWAX high performance anion exchange column equilibrated at 1.5 ml/min in 0.05 M ammonium hydrogen carbonate (unadjusted pH=7.8). The ALS was eluted by applying a linear salt gradient (Model 680 Gradient Controller, Waters, Milford, Mass.) from 0.05 M to 0.5 M ammonium hydrogen carbonate (pH adjusted) over 15 min at 1.5 ml/min. In some preparations a concave gradient was used (gradient #7, Model 680 Gradient Controller) over the same concentration range, with comparable results. Absorbance at 280 nm was monitored using a Waters Model 441 Absorbance Detector. Fractions of 0.75 ml were collected and assayed for ALS activity. A single major protein peak emerged from the column after 9–10 min elution at 1.5 ml/min when a linear gradient was employed, or 11–12 min using a concave gradient. All of the detectable ALS activity, determined by RIA, was associated with this peak, with the recovery of applied activity estimated at over 75%, and a further increase in specific activity of 1.6-fold. The ALS activity was always associated with a single peak.

FIG. 2 shows purified ALS after HPLC fractionation electrophoresed on a linear 10–15% polyacrylamide gel, under both reducing and non-reducing conditions. The preparation appeared as a doublet of apparent molecular mass 84 and 86 KDa under either non-reducing (left panel) or reducing conditions. Acidification of the protein (prepared by adjusting 35 $\mu$g of ALS in 50 $\mu$l 0.05M ammonium hydrogen carbonate to pH 3 with 20 $\mu$l of 1M acetic acid, incubating 15 min. at 22° C., and neutralizing with 10 $\mu$l of 2M Tris base), which results in a substantial loss of activity, had no effect on the protein's mobility on SDS-PAGE when run either non-reduced or reduced. However, treatment with N-glycanase (25 $\mu$g ALS boiled in 40 $\mu$l 0.5% SDS for 3 min., then diluted in 0.55 M Na phosphate, pH 8.6 and Nonidet P-40 to final concentrations of 0.2 M and 1.25% respectively; then N-glycanase (Genzyme Corp., Boston, Mass.) was added to a final concentration of 60 units/ml, and the mixture incubated at 16 h at 27° C.) to remove N-linked carbohydrate resulted in a significant decrease in apparent molecular mass, to 80 kDA non-reduced (left panel) and 66 kDA (right panel). Notably, the protein migrated as a single band after deglycosylation with N-glycanase, suggesting that the doublet seen in the native preparation is due to at least two glycosylation variants. Under reducing conditions, the deglycosylated preparation showed several bands in the range 50–60 kDa, suggesting that further deglycosylation might be possible.

Table 1 summarizes the results of a typical ALS purification, one of four performed on a similar scale and with similar results. Fractions eluted from the DEAE-Sephadex column by 0.05 M Tris-HCl, 0.6 M NaCl, pH 8.2 (DEAE eluate #2), contained over 60% of the applied ALS immunoreactivity and 13% of the total protein, whereas fractions eluted with buffer containing 0.15 M NaCl (DEAE eluate #1) contained only 15% of the ALS activity, but 79% of the protein. Further purification of DEAE eluate #2 fractions by affinity chromatography on a column of BP-53 non-covalently bound to agarose-IGF yielded a 200-fold increase in ALS specific activity.

The purification strategy employed was constrained by the fact that the sub-unit is irreversibly inactivated at low pH, but took advantage of the fact that it is reversibly dissociated from the BP-IGF complex at high pH. The key step in the purification is an unusual application of affinity chromatography in which the affinity ligand (BP-53) is not attached to the agarose matrix by a covalent bond, but appears to act as a non-covalent bridge between agarose-IGF beads and the ALS. In retrospect it is clear that the use of a covalent agarose-BP-53 matrix would not have worked, since BP-53 unoccupied IGF-I or IGF-II is unable to bind ALS. The optional final step, high performance chromatography on a PolyWAX (weak anion-exchange) column with salt gradient elution, essentially reiterates the initial step of DEAE-Sephadex chromatography, but at much higher resolution.

Example 3

Amino-terminal Sequence of ALS:

The N-terminal sequence of ALS was determined on an estimated 35 $\mu$l sample of HPLC purified material by Edman degradation using an Applied Biosystems 470A automatic gas-phase protein sequencer coupled to a 120A PTH Analyzer using a standard PTH program. Cys residues were confirmed on a second sample after reduction with mercaptoethanol and carboxymethylation with iodoacetic acid.

In two determinations, amino-terminal analysis showed approximately equimolar amounts of Gly and Ala for the first residue, despite the fact that the preparation analyzed was from the serum of a single donor. Analysis of the first 18 residues yielded the sequence Gly(Ala)-Asp-Pro-Gly-Thr-Pro-Gly-Glu-Ala-Glu-Gly-Pro-Ala-Cys-Pro-Ala-Ala-Cys-, the Cys residues in positions 14 and 18 being confirmed on a reduced and carboxymethylated sample. This amino acid sequence shows no obvious homology to other IGF proteins or receptors.

Example 4

DEAE-Sephadex Fractionation of Serum:

The starting material was an ammonium sulfate fraction of serum from 30–50% saturation prepared according to previously published tables (Green, A. A., and Hughes, W. L., Methods of Enzymol. 1, 67). The resulting precipitate, dialyzed against an excess of 50 mmol/L Tris-HCl, pH 8.2, contained approximately 75% of the BP-53 immunoreactivity of whole serum. In subsequent studies, the ammonium sulfate fractionation was found to be unnecessary, and whole serum dialyzed against Tris-HCl buffer was used. A 1×17.5 cm. column of DEAE-Sephadex A-50, equilibrated in 50 mmol/L Tris-HCl, pH 8.2, was loaded with a 1-mL dialyzed sample and eluted with 35 mL starting buffer, 50 mL starting buffer plus 0.15 mol/L NaCl, and 50 mL starting buffer plus 0.6 mol/L NaCl. In a larger scale protocol, 10-mL dialyzed samples were loaded onto a 1.5×20 cm column and eluted with 50, 100 and 100 mL, respectively, of the three buffers. The major protein peak eluting in the presence of 0.15 mol/L NaCl was termed peak A, and the peak emerging in 0.6 mol/L NaCl was termed peak B (FIG. 3).

The majority of immunoreactive BP-53 was found in the first peak (peak A), whereas the second peak (peak B) contained ALS activity with very little BP-53 immunoreactivity (FIG. 3 bottom). A small amount of ALS activity also was detected in fractions corresponding to the descending side of peak A (not shown). Similar results were obtained in six separate experiments.

FIG. 4, representative of three similar experiments, shows the BP-53 immunoreactivity profiles for these protein peaks, separately and after preincubation together when fractionated by Superose-12 chromatography. The BP-53 immunoreactivity from peak A eluted primarily in a broad peak between fractions 25 and 30, corresponding to a molecular mass range of approximately 30–60K, with a small peak in fractions 22–24; corresponding to 150K (FIG. 4a). The barely detectable BP-53 activity from peak B eluted from Superose-12 predominantly in fractions 23–25 (FIG. 4b). After mixing peaks A and B and preincubating for 60 min at 22° C., over 50% of the peak A BP-53 activity had shifted from 30–60K to 150K, with the remainder still at 30–60K (FIG. 4c). This may be compared with the BP-53 profile in whole serum, in which over 90% of the activity was at 150K and only 5–10% in the 30–60K region (FIG. 4d). The ALS activity of peak B, as depicted in FIG. 4c, was unaffected by dialysis of peak B fractions against Tris buffer containing no NaCl or 0.6 mol/L NaCl, indicating that neither high salt nor any other dialyzable molecule was involved in the reaction between BP-53 and the ALS in peak B.

Superose-12 Fractionation of Serum:

Serum from normal subjects was diluted 1:1 with 50 mmol/L sodium phosphate, 0.15 mol/L NaCl, and 0.2 g/L sodium azide, pH 6.5, and 200 μL was applied to the Superose-12 column and eluted as described for the routine ALS assay. Each fraction was then tested for BP-53 and ALS activity.

As shown previously in FIG. 4d, BP-53 immunoreactivity peaked in fraction 23, corresponding to 150K (FIG. 5). In contrast, in three experiments the peak ALS activity reproducibly eluted in fraction 24 (FIG. 5), corresponding to 90–110K, suggesting that there is an excess of ALS over BP-53 in serum and that the free sub-unit has an apparent molecular mass of 90–110K. A similar peak of ALS activity was found in serum from which more than 99% of immunoreactive BP-53 (i.e. essentially all of the 150K complex) had been removed by affinity chromatography on a column of anti-BP-53 antibody coupled to agarose (not shown), confirming that the ALS detectable at 90–110K was not complexed to BP-53. A comparable result was found when serum was fractionated by ion exchange chromatography, as shown in FIG. 3 and peak B was subjected to Superose-12 chromatography.

Increasing volumes of serum when tested in the routine ALS assay, gave a dose dependent increase in the 150 K/60K ratio (not shown). The ALS detectable in whole serum appeared to be GH dependent, as higher activity was found in serum from five acromegalic subjects and lower activity in serum from five GH-deficient subjects than was detectable in samples from normal subjects. This GH-dependence provides the basis for a diagnostic assay for determining GH levels in serum, and may be exploited in the diagnosis of growth disorders using, for example, antibodies directed against ALS.

Example 5

Acid lability of ALS:

The acid lability of purified ALS or ALS in whole serum (following procedure of Example 2) was evident by its irreversible inactivation on exposure to low pH. The protein appeared quite stable at pH values as low as 5, but below this it rapidly lost activity (FIG. 7); and the 150K/60K ratio decreased by over 80% at pH 3. This decrease in the 150K/60K ratio is equivalent to a decrease in apparent ALS activity of over 99%. In contrast, exposure at high pH values (up to pH 10) had no effect on ALS activity in whole serum or the purified preparation.

Example 6

Functional Studies:

To determine the binding kinetics of ALS to BP-53, incubations were set up containing [$^{125}$I]-labeled ALS and various concentrations of BP-53 and IGF-I or IGF-II. Complexes of ALS tracer with BP-53 were detected after immunoprecipitation using an antiserum against BP-53 which has previously been shown to react with the BP in both free and complexed forms (Baxter, R. C. and Martin, J. L. (1986) J. Clin. Invest. 78, 1504–1512). FIG. 7 (left) shows the effect of increasing BP-53 concentrations, over the range 0.25 to 100 ng/tube (0.016 to 6.3 nM), on complex formation. In the absence of IGF-I or IGF-II, there was little or no reaction between ALS tracer and BP-53. In the presence of a molar excess of IGF-I or IGF-II (50 ng/tube or 22 nM), a dose-dependent increase in ALS tracer binding was seen, increasing to 50% specific binding to 100 ng/tube of BP-53. Higher concentrations of BP-53 could not be tested due to limitations of the immunoprecipitation system. Complex formation was consistently higher in the presence of IGF-I than IGF-II.

The binding affinity between ALS and BP-IGF complexes was estimated from competitive binding studies. As shown for a typical experiment in FIG. 7 (right), binding of [$^{125}$I]-labeled ALS was again greater in the presence of IGF-I than IGF-II. In three similar experiments, the mean specific binding (±SEM) to 10 ng/tube BP-53 (i.e. corrected for radioactivity precipitated in the absence of BP-53) was 24.3±4.4% in the presence of excess IGF-I, and 19.6±3.9% in the presence of excess IGF-II (P=0.009 by paired t-test). Increasing concentrations of unlabelled ALS caused a dose-dependent displacement of [$^{125}$1I]-labeled ALS from immunoprecipitatable complexes. Analysis of binding data by Scatchard plot revealed a nonspecific binding component (association constant $<10^6$ M$^{-1}$) and a single specific binding component with a slightly higher affinity for BP-IGF-I than BP-IGF-II. In three similar experiments the mean association constant (±SEM) for ALS binding to BP-IGF-I was $6.06±0.71×10^8$ M$^{-1}$, and for ALS binding to BP-IGF-II, $4.12±0.29×10^8$ M$^{-1}$. The binding site concentration was 1.28±0.46 mol ALS/mol BP-53 in the present of IGF-I, and 1.18±0.29 mol/mol in the presence of IGF-II, assuming the molecular masses of ALS and BP-53 are 86 kDa and 53 kDa respectively. If the calculation is based on the reduced molecular mass of 43 kDa for BP-53, the binding site concentrations are 1.04±0.37 mol/mol and 0.96±0.33 mol/mol respectively. This result is consistent with a single binding site for ALS per molecule of BP-53.

The lack of effect of ALS on the interaction between BP-53 and the IGFs is shown in FIG. 8. [125I]-labeled IGF-II consistently showed higher binding to increasing concentrations of BP-53 than [$^{125}$I]-labeled IGF-I. The binding of either tracer was unaffected by the addition of 100 ng pure ALS per tube (FIG. 8, left). Competitive binding curves for the displacement of [$^{125}$I]-labeled IGF-II from BP-53 by increasing concentrations of unlabelled IGF-I and IGF-II are shown in FIG. 8 (right). IGF-II was consistently more potent than IGF-I in displacing tracer from BP-53, and neither displacement curve was affected by the addition of 100 ng/tube of ALS. Similar results were seen when [$^{125}$I]-labeled IGF-I was used as tracer (not shown).

To confirm that pure ALS was capable of converting the BP-53 to the 150 kDa form, incubation mixtures similar to those used in the competitive binding experiments shown in FIG. 8 were fractionated by gel chromatography on Superose 12. [$^{125}$I]-labeled IGF-II appeared as a single peak of radioactivity, peaking in Fraction 34. Incubation of this tracer with pure ALS (100 ng/200 μL) before fractionation had no effect on the radioactive profile, indicating that ALS alone was unable to bind IGF-II tracer (FIG. 9, left). Incubation of IGF-II tracer with 1 ng/200 μl pure BP-53 resulted in the conversion of 70% of the radioactivity to a 60 kDa form, i.e. BP-53—IGF-I. When this incubation also included 100 ng/200 μl pure-ALS, the 60 kDa complex was substantially converted to a 150 kDa form (FIG. 4, right), demonstrating that complex formation required no components other than pure IGF, pure BP-53, and pure ALS.

Example 7
Inhibition of ALS Binding to BP-53—IGF-I:

Various substances were tested for their ability to inhibit tracer BP-53—IGF-I binding to ALS. Human serum, when acidified and reneutralized to destroy its endogenous ALS activity and leave its acid-stable BP-53 intact, contained potent competing activity. On comparing samples from normal, acromegalic, and GH-deficient subjects in this way in three separate experiments, the competing activity showed strong GH-dependence, as expected for the endogenous BP-53 in such samples. This is illustrated for one such experiment in FIG. 10a. When the curves in FIG. 8a were replotted in terms of the immunoreactive BP-53 content of each sample, they became superimposable (FIG. 10b), indicating that the endogenous BP-53 in acidified whole serum could compete with cross-linked tracer in the ALS reaction. Under the conditions used in this assay, approximately 1 μg BP-53/mL reaction volume (i.e. 250 ng/250 μL) fully displaced cross-linked tracer from the BP-ALS complex, with half-maximal displacement at 200–250 ng/mL BP-53.

In contrast to the endogenous BP-53 in acidified serum, pure BP-53, when tested at up to 0.8 μg/mL, was unable to compete with cross-linked tracer in the ALS reaction (FIG. 11). However, after preincubation for 30 min at 22° C. with a 3.5-fold molar excess of pure human IGF-I or IGF-II (i.e. 500 ng IGF/μg BP-53), purified BP-53 could fully displace cross-linked tracer from the BP-53-ALS complex. Also tested, and found not to compete in the ALS reaction, were the following; purified amniotic fluid BP-28 (0.8 μg/mL), BP-28 preincubated with excess IGF-I or IGF-II (0.5 μg/mL), or human GH (20 μg/mL). These experiments again indicate that only BP-53 that is occupied by IGF-I or IGF-II can take part in the reaction with ALS and strongly suggest that BP-28, whether occupied or not, is unable to react with ALS.

The scientific articles previously referred to are incorporated herein in their entirety.

The claims form part of the description.

TABLE 1

Purification of the acid-labile subunit
from human serum
The purification steps were as described in Example 2.
ALS, determined by radioimmunoassay, is expressed in terms of a pure standard preparation. DEAE eluate #1 refers to the pool of fractions eluted from DEAE-Sephadex by buffer containing 0.15 M NaCl. DEAE eluate #2 refers to the pool of fractions eluted by buffer containing 0.5 M NaCl; this pool was dialyzed before assay. Affinity eluate is the pool of fractions eluted from the affinity column, then concentrated by ultrafiltration. HPLC pool is the pool of active fractions recovered from the HPLC step.

| Purification Step | Volume ml | Total Protein mg | Total ALS μg | ALS specific Activity μg/mg protein | Purification Factor fold | Recovery % |
|---|---|---|---|---|---|---|
| Serum | 120 | 11860 | 8290 | 0.70 | 1.0 | 100 |
| DEAE eluate #1 | 2530 | 9360 | 1280 | 0.14 | 0.2 | 15.4 |
| DEAE eluate #2 | 132 | 1530 | 5060 | 3.31 | 4.7 | 61.0 |
| Affinity eluate | 4.5 | 2.61 | 1850 | 709 | 1010 | 22.3 |
| HPLC pool | 15.75 | 1.22 | 1400 | 1148 | 1640 | 16.9 |

What is claimed is:

1. A method for increasing the half-life of insulin-like growth factor in vivo in animals or humans, said method comprising:

administering to said animal or human a therapeutically effective amount of a composition comprising a purified acid-labile subunit (ALS) of insulin-like growth factor binding protein complex, wherein in vivo, the ALS is in complexed form with insulin-like growth factor-I and acid-stable insulin-like growth factor binding protein, whereby the half life of insulin-like growth factor in vivo is increased, and wherein said ALS comprises a partial N-terminal amino acid sequence comprising: Gly AspProGlyThrProGlyGluAlaGluGlyProAlaCysProAlaAlaCysAla wherein the first amino acid may be Gly or Ala (SEQ ID NOs:1 and 2, respectively, with SEQ ID NO:1 starting with Gly and SEQ ID NO:2 starting with Ala).

2. The method of claim 1 wherein insulin-like growth factor-I is administered in the composition comprising the ALS.

3. The method of claim 1 wherein the acid-stable insulin-like growth factor binding protein is administered in the composition comprising ALS.

4. The method of claim 1 wherein the insulin-like growth factor-I and acid stable insulin-like growth factor binding protein are administered in the composition comprising ALS.

5. The method of claim 4 wherein the ALS, insulin-like growth factor-I and binding protein are biologically pure.

6. The method of claim 4 wherein the ALS, insulin-like growth factor-I and binding protein are complexed prior to administration.

* * * * *